US006235518B1

(12) United States Patent
Gicquel et al.

(10) Patent No.: US 6,235,518 B1
(45) Date of Patent: May 22, 2001

(54) RECOMBINANT IMMUNOGENIC ACTINOMYCETALE

(75) Inventors: Brigitte Gicquel; Nathalie Winter, both of Paris; Marina Gheorghiu, Neuilly-sur-Seine, all of (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 08/157,152

(22) PCT Filed: Jun. 12, 1992

(86) PCT No.: PCT/EP92/01343

§ 371 Date: Jul. 26, 1994

§ 102(e) Date: Jul. 26, 1994

(87) PCT Pub. No.: WO93/25678

PCT Pub. Date: Dec. 23, 1993

(30) Foreign Application Priority Data

Jun. 14, 1991 (GB) ............................................... 91401601

(51) Int. Cl.[7] .............................. C12N 1/12; C12N 1/20; A61K 39/04; C07H 21/02

(52) U.S. Cl. .................................... 435/253.1; 435/252.1; 424/248.1; 424/204.1; 424/188.1; 536/23.1

(58) Field of Search ...................... 435/253.1; 424/248.1, 424/204.1, 188.1; 536/23.1

(56) References Cited

U.S. PATENT DOCUMENTS 5,591,632 1/1997 O'Donnell et al. ............... 435/252.3
5,736,367 * 4/1998 Haun et al. .
5,843,664 * 12/1998 Pelicic et al. .
5,869,233 * 2/1999 Crowl et al. .
5,877,273 * 3/1999 Hance et al. .

FOREIGN PATENT DOCUMENTS 0 400 973 12/1990 (EP) .
WO 90/00594 1/1990 (WO) .
WO 90/10701 9/1990 (WO) .
WO 90/15873 12/1990 (WO) .
WO 91/04051 4/1991 (WO) .
WO 92/01796 2/1992 (WO) .

OTHER PUBLICATIONS

Res. Microbiol., vol. 141, No. 7,8, pp. 931–939, 1990, R.G. Barletta, et al., "Recombinant BCG as a candidate oral vaccine vector".

Bahraoui, et al, 1990, "Immunogenicity of the human . . . ", AIDS Res Hum. Retro. :6(9): 1087–98.*

Guy, et al, 1987, "HIV F/3'of encodes a . . . " Nature 330: 266–269.*

Carol A. Gross et al: "The Function and Regulation of Heat Shock Proteins in *Escherichia coli*", Stress Proteins in Biology and Medicine, Chapter 8, 1990, pp. 167–189.

* cited by examiner

*Primary Examiner*—Nita Minnifield
(74) *Attorney, Agent, or Firm*—Oblon, Spivak, McClelland, Maier & Neustadt, P.C.

(57) ABSTRACT

A mycobacteria transformed with an antigen-encoding gene, such as nef, under the control of a Streptomyces stress-responsive promoter, such as the *S. albus* groES/groEL1 promoter, and preferably associated with a synthetic ribosome binding site. The recombinant mycobacteria can be used as a vaccine against, for example, a pathogen which carries the antigen.

31 Claims, 6 Drawing Sheets

RECOMBINANT IMMUNOGENIC ACTINOMYCETALE

Figure 1:
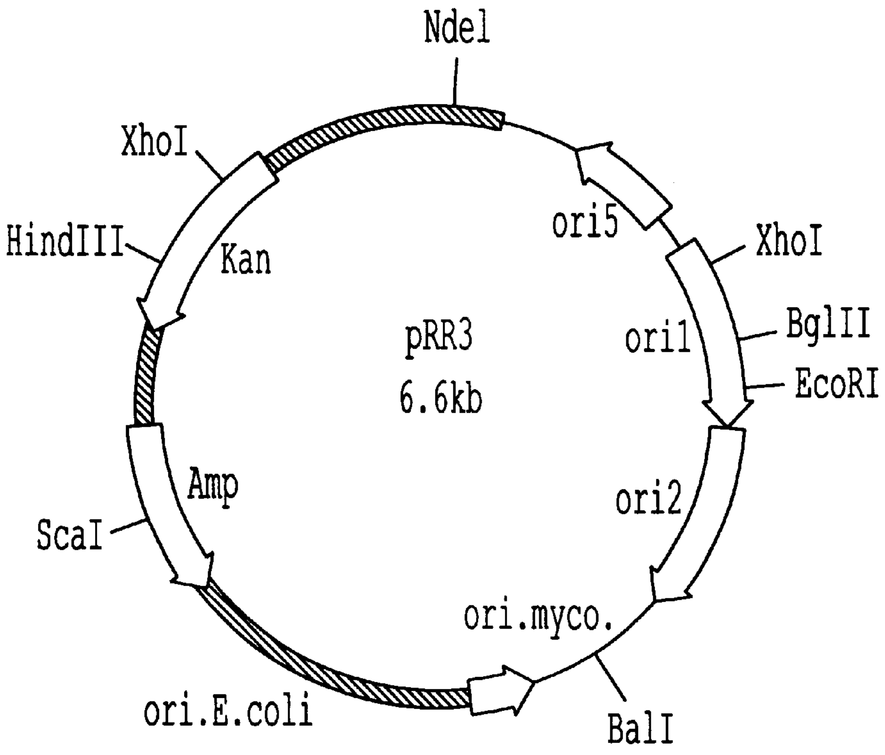

This invention relates to a strain of a species of Actinomycetale (the "Actinomycetale strain"), particularly a strain of mycobacteria, which: a) has been transformed with at least one gene or a DNA fragment thereof (an "antigen-encoding gene") that codes for all or at least part of an antigen, particularly at least one epitope thereof (a "desired antigen", preferably a "immunizing antigen"); and b) can be used to inoculate mammals, particularly humans, to immunize them, preferably protect them (e.g., from a pathogen carrying all or part of the desired antigen). In this regard, the term "desired antigen" comprises any molecule which is capable of inducing an immune response, including a protein, glycoprotein, glycolipoprotein, peptidoglycolipid, etc., or an immunogenic fragment thereof, and which can, for example, come from, or be derived from, a pathogen against which the transformed Actinomycetale strain is to provide an immunity, preferably a protection.

BACKGROUND OF THE INVENTION

Various types of vaccines have been developed against pathogens. When a humoral immune response is able to confer protection, subunit or killed vaccines are efficient. However, in the case of tuberculosis and certain other infectious diseases, killed pathogens are not protective.

The vaccine currently used to protect against tuberculosis, *Mycobacterium bovis* BCG (Bacille Calmette-Guerin) or "BCG", is the unique live bacterial vaccine in use. *M. bovis* BCG and all other mycobacteria survive in macrophages which are antigen-presenting cells and initiate the humoral and T-cell mediated immune response (EDWARDS and KIRKPATRICK, 1986). This might explain the stimulant activities of this vaccine. *M. bovis* BCG offers many advantages for development of a recombinant polyvalent vaccine vector expressing antigens from a wide variety of pathogens, particularly those in which cell-mediated immunity is important for protection (BLOOM, 1986; JACOBS et al, 1988). It is an attenuated *M. bovis* strain which has been used without major side effects to vaccinate more than two billion people, it is produced at low cost, and it can be given at birth as a single dose and is then able to confer long term immunity. It also has stimulant activities and has been used as an adjuvant in various protocols of immunization.

The recent development of genetic tools for transforming mycobacteria has enabled the cloning of foreign genes in both fast-growing (*M. smegmatis*) and slow-growing (*M. bovis* BCG) strains. Several phasmid-and plasmid-based vectors have been reported, for example in PCT publication WO88/06626. Starting from pAL5000, a plasmid from *M. fortuitum* whose entire nucleotide sequence has been determined (RAUZIER et al, 1988), various *E. coli*-mycobacteria shuttle plasmids have been constructed which stably replicate in mycobacteria, including a "mini" mycobacterial replicon, pRR3 (RANES et al, 1990). Foreign genes have been cloned on these vectors and on other integrative vectors described in STOVER et al (1991) and shown to be expressed in mycobacteria using their own control elements or as fused genes (MATSUO et al, 1990).

SUMMARY OF THE INVENTION

This invention provides an immunogenic Actinomycetale strain, particularly a strain of mycobacteria, transformed with the following, operably linked, chimaeric DNA sequence, comprising an antigen-encoding gene that: a) is foreign to the Actinomycetale strain; b) encodes a desired antigen, preferably an immunizing antigen; c) is under the control of a promoter foreign to the Actinomycetale strain, preferably a promoter from another strain of Actinomycetale, especially a promoter from another species of Actinomycetale, particularly a Streptomyces promoter, quite particularly a stress-responsive (e.g., heat-shock) promoter; and d) is preferably associated with a ribosome binding site ("RBS") foreign to the Actinomycetale strain, particularly foreign to Actinomycetale and/or synthetic.

This invention also provides the aforementioned chimaeric DNA sequence, especially wherein the antigen-encoding gene codes for an HIV-1 protein (European patent publications ("EP") 0 178 978 and 201,540) or an HIV-2 protein (EP 0 239 425), particularly a Nef protein (e.g., the Nef 1 protein of HIV-1 or Nef 2 protein of HIV-2), or an antigenic fragment or an epitope thereof which can induce an immune response in a mammal, particularly a T or B response, quite particularly wherein the antigen-encoding gene is under the control of the *S. albus* groES/groEL1 promoter.

This invention further provides a system, such as a plasmid, capable of transforming a Actinomycetale strain. This system comprises a foreign promoter, a foreign ribosome binding site and a DNA fragment coding for an antigen foreign to the Actinomycetale strain, particularly the aforementioned chimaeric DNA sequence, quite particularly pWRIP17.

This invention yet further provides: a) an immunogenic composition, particularly a vaccine, comprising the aforementioned transformed Actinomycetale strain, particularly a strain of mycobacteria, quite particularly BCG, and if necessary, a suitable carrier, as well as, for example, an adjuvant for human use; and b) a method of immunizing a mammalian host, particularly a human, against, for example, a pathogen, comprising the step of administering to the host the aforementioned composition.

This invention also provides: a) a process to produce the desired antigen by culturing the transformed Actinomycetale strain; and b) a process for using the desired antigen or the transformed Actinomycetale strain, for example, as a diagnostic agent and/or an immunogenic agent. An antigenic preparation containing the desired antigen or the transformed Actinomycetale strain can induce the synthesis of specific antibodies or cellular reactions in in vitro and in vivo diagnostic tests and immunogenic treatments.

DETAILED DESCRIPTION OF THE INVENTION

In accordance with this invention, a recombinant immunogenic strain of a species of Actinomycetale, such as Actinomycetaceae and Mycobacteriacae, especially Corynebacteria, Streptomyces and Mycobacteria, particularly Mycobacteria, can be obtained by transforming the Actinomycetale strain with the operably linked chimaeric DNA sequence of this invention.

The antigen-encoding gene of the chimaeric DNA sequence or expression cassette, used to transform the Actinomycetale strain in accordance with this invention, can be any gene or DNA fragment thereof which encodes a desired antigen as hereinbefore defined, whose expression products can be used, for example, to induce an immune response, preferably in a vaccine administered to a mammalian host, preferably a human, to immunize and preferably protect the host, for example, against a pathogen. Pathogens, whose immunizing antigens can be encoded by the antigen-encoding gene, include, for example, viral, parasitic and bacterial, particularly viral, pathogens such as *M. leprae, M. tuberculosis, M. intracellulare, M. africanum, M. avium*, plasmodium sporozoites and merozoites, diphtheria toxoid, tetanus toxoids, Leishmania, Salmonella, some Treponema, pertussis toxin and other antigenic determinants and viruses, including measles, mumps, herpes, influenza, Schistosoma, Shigella, Neisseria, Borrelia, rabies, polio virus, hepatitis virus, human immunodeficiency viruses (HIV), HTLV-I, HTLV-II, and Simian immunodeficiency virus (SIV), as well as oncogenic viruses. Alternatively, the antigen-encoding gene can encode an immunizing antigen from other than a pathogen, such as a snake or insect venom. In this regard, this invention is not limited to the expression of desired antigens for immunizing a mammal against a pathogen but also includes the use of the transformed Actinomycetale strain of this invention for the development of other kinds of immunotherapy treatments, as well as for the production of molecules of interest. For example, the transformed Actinomycetale strain, cloned with a gene coding for the synthesis of a hormone, could be used in an anti-fertility vaccine, or the transformed Actinomycetale strain, cloned with a tumor-associated gene such as an oncogene, could be used in an anti-cancer vaccine.

The promoter, which is upstream (i.e., 5') of, and used to control, the antigen-encoding gene in the chimaeric DNA sequence of this invention is critical to this invention in providing high levels of expression of the gene in Actinomycetale, particularly mycobacteria. The promoter can be any promoter from a strain different from that of the Actinomycetale strain being transformed but is preferably from a different strain of Actinomycetale, particularly from a different species of Actinomycetale. Preferably for the transformation of mycobacteria, the promoter is a Streptomyces promoter. The promoter is also preferably a stress-responsive promoter, especially a heat-shock promoter, particularly an Actinomycetale promoter, quite particularly a groEL promoter or a groEL-like promoter of French patent application 9011186, filed Sep. 10, 1990 (which is incorporated herein by reference). A copy of the Disclosure and Figures of French application 9011186 is appended hereto as "Appendix A", following the list of references.

However, other promoters, not from Actinomycetale, can also be used in the chimaeric DNA sequence of this invention. For example, a phage lambda (pL) promoter (GUY et al, 1987) or a promoter of an antibiotic resistance gene, such as the bacterial promoter of the kanamycin resistance gene (OKA et al, 1981), the bacterial promoter of the sulfonamide gene (MARTIN et al, 1990) or the bacterial TAC promoter (AMRANN et al, 1983), as well as the promoters of other bacterial genes, can be used.

The chimaeric DNA sequence of this invention optionally includes, downstream (i.e., 3') of the promoter and upstream of the antigen-encoding gene, a ribosome binding site (RBS) which is preferably synthetic or foreign to the Actinomycetale strain, particularly the Actinomycetale species, being transformed. It is particularly preferred that the ribosome binding site be foreign to Actinomycetale, generally, and quite particularly preferred that the ribosome binding site for transforming mycobacteria be the synthetic ribosome binding site of the *E. coli* plasmid pTG1166 (GUY et al, 1987). This particularly preferred RBS has the following sequence: 5'ATCGATAACAGAGGAACAGATCT3', (SEQ ID NO:1)

Preferably associated with the chimaeric DNA sequence of this invention in the recombinant Actinomycetale strain is a selectable marker gene, such as an antibiotic resistance-encoding gene, for example a gene encoding kanamycin resistance, viomycin resistance, thiostrepton resistance, hygromycin resistance or bleomycin resistance, in order to make it possible to identify and isolate recombinant Actinomycetale strains of this invention. A conventional selectable marker can be used such as is described in PCT publication WO 88/06626 and in European patent publication ("EP") 400,973. The selectable marker gene is preferably in the same genetic locus as the chimaeric DNA sequence of this invention in any plasmid, phasmid or shuttle vector used to transform the Actinomycetale strain. For good expression of the selectable marker gene, it can be driven by the same types of promoter and/or ribosome binding site used in the chimaeric DNA sequence of this invention to obtain good expression of the antigen-encoding gene. However, this is not believed necessary, and the endogenous promoter and RBS of the marker gene or of other promoters, conventionally used with the marker gene, can generally be suitably utilized.

An Actinomycetale strain, particularly a strain of mycobacteria, can be transformed with the chimaeric DNA sequence of this invention, as well as a marker gene, in a conventional manner. In this regard, the strain of Actinomycetale can be transformed by incorporating the chimaeric DNA sequence of this invention into a suitable *E. coli*/Actinomycetale shuttle vector and then subjecting the vector and the Actinomycetale strain to electroporation. For example, the electroporation procedures of GICQUEL-SANZEY et al (1989) and RANES et al (1990) can be suitably used, as well as the procedures generally described in EP 400,973. Alternatively, the chimaeric DNA sequence of this invention can be incorporated: into a shuttle phasmid and used to transform an Actinomycetale, particularly a mycobacteria, strain in accordance with PCT publication WO 88/06626; into a secretory expression vector and used to transform an Actinomycetale strain in accordance with EP 400,973; into a conjugative plasmid used to transform the Actinomycetale strain in accordance with LAZRAQ et al (1990); or by transposition using a vector for transposon delivery (i.e., with an integrative plasmid, replicative plasmid or phage).

The recombinant immunogenic Actinomycetale strain of this invention can be used in an immunogenic composition, preferably a vaccine, for example, to render a mammal, particularly a human, resistant to a pathogen of the immunizing antigen encoded by the antigen-encoding gene of the chimaeric DNA sequence of this invention. Preferably, the recombinant Actinomycetale strain is a live non-pathogenic strain such as *M. bovis* BCG or is a strain which has been inactivated, for example by heating it or by treating it with formalin, if necessary. The recombinant Actinomycetale strain can then be mixed with a conventional pharmaceutically acceptable vehicle, such as a physiological saline solution, together with conventional excipients, such as sodium glutamate, carbohydrates, glycerol, amino acids, detergents etc., to form a vaccine. The vaccine can be formulated to contain a final concentration of cell material in a range of 0.2 to 5 mg/ml, preferably 0.5 to 2 mg/ml. After formulation, the vaccine can be placed in a sterile container, which is then sealed and stored at a low temperature (e.g., 4° C.), or it can be freeze-dried or fresh frozen.

In order to induce immunity in a human host, one or more doses of the vaccine, preferably just one suitably formulated dose, can be administered in doses each containing about $10^5$–$10^7$, preferably about $10^6$, cells. The vaccine can be administered. by different routes, for example by intradermal (ID), subcutaneous (SC), percutaneus, oral, spray or aerosol routes.

The Examples, which follow, involve the construction of vectors providing an efficient expression in *M. bovis* BCG of the HIV-1 gene encoding the Nef protein ("Nef") as an example of an eucaryotic viral gene. The HIV-1 Nef-encoding gene ("nef") is used as a model to study gene expression and induction of a cellular immune response by a recombinant *M. bovis* BCG vaccine of this invention. Nef is a 27 kD regulatory protein encoded by a single open reading frame which overlaps the 3' long terminal repeat (LTR). Nef is myristilated and localized in the cytoplasm associated with the inner face of the HIV-1 cellular membrane (GUY et al, 1987). Nef is expressed at an early stage of the HIV infection and is involved in the down-regulation of CD4 cell-surface receptors of permissive T4 lymphocytes (GUY et al, 1987; GARCIA and MILLER, 1991). CTL (RIVIERE et al, 1989; CULMANN et al, 1989) has been detected in HIV seropositive donors. It is believed that the recombinant *M. bovis* BCG vaccine of the Examples, expressing Nef, could induce the destruction of infected cells which express Nef at an early stage of HIV infection, before HIV can release newly synthesized viral particles. This would be a desirable result from a vaccine.

The results of the Examples show that the promoter of the groES/groEL1 operon from *S. albus* can be used to express the HIV-1 Nef protein in recombinant nef-BCG. The HIV-1 nef gene was cloned on a replicative plasmid derived from pRR3 (FIG. 1) and expressed under the control of the pL promoter of phage lambda and the promoter of the groES/groEL1 operon of *Streptomyces albus* to accumulate the Nef protein in the BCG cell. The groES/groELI promoter provided a high level of Nef expression in *M. bovis* BCG. As a result, a high and specific proliferative response of lymph node cells was induced in mice inoculated with the immunogenic recombinant mycobacteria in which the promoter of the chimaeric DNA sequence of this invention was the groES/groEL1 promoter. In this regard, the total amount of Nef protein was estimated to be 1% of the total cellular protein, but no degradation of Nef was observed, and lymph node cells from mice immunized with nef-BCG strongly proliferated in response to purified Nef protein.

The Figures referred to in the Examples are as follows:

FIG. 1. Schematic structure of the "mini" *E. coli*-mycobacteria shuttle cloning vector pRR3 of Example 1. A thin line shows the 2.58 kb fragment from pAL5000 (RANES et al, 1990). Sequences from pUC19 are shown as a thick line. Origins of replication for *E. coli* and mycobacteria are shown. This plasmid contains the ApH (3') phosphotransferase-encoding gene from Tn903, conferring resistance to kanamycin ("$Kan^r$"), and the ampicillin resistance ("$Amp^r$") gene from pBR322.

Figure 2:
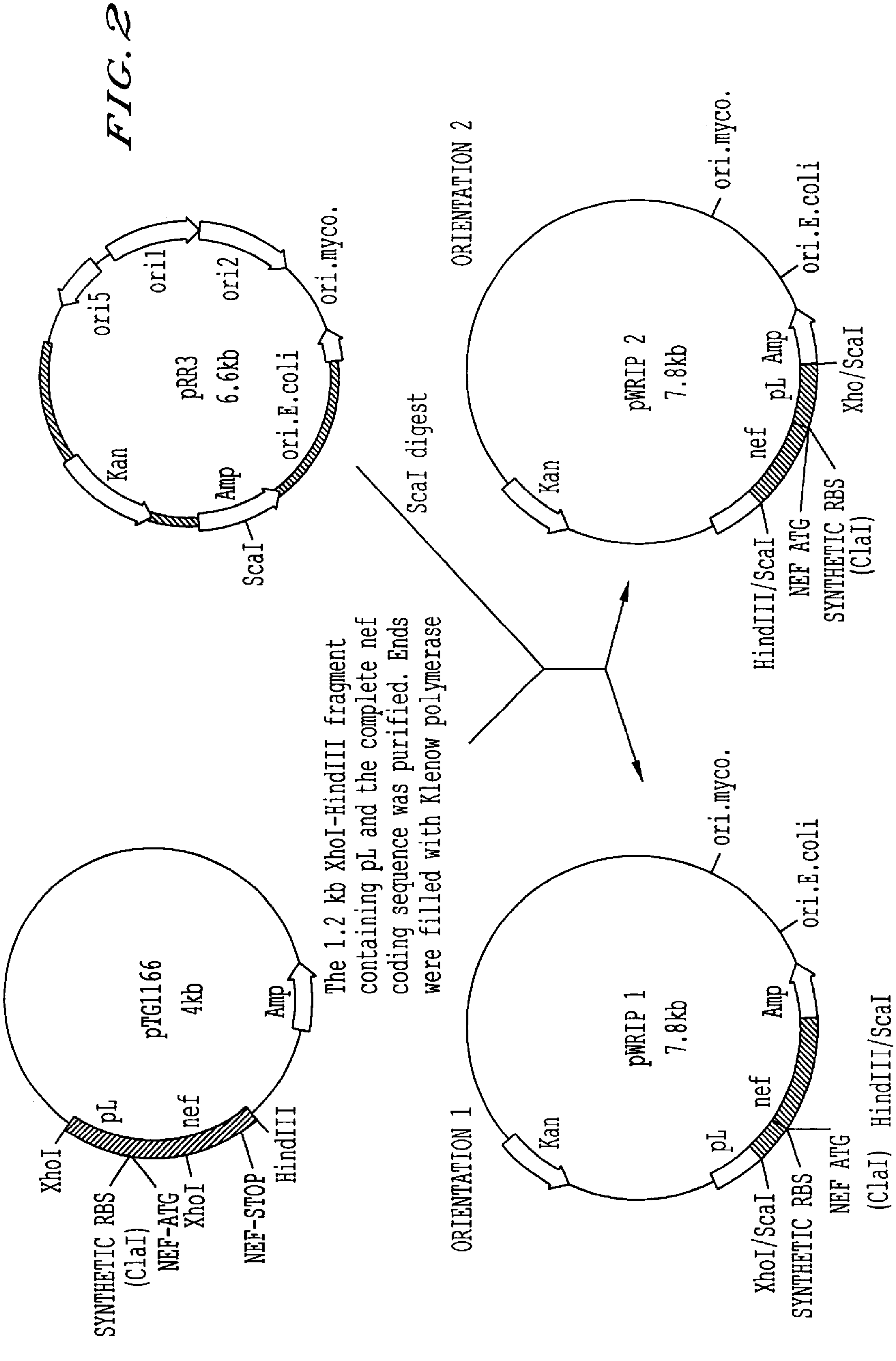

FIG. 2. Construction of pWRIP1 and pWRIP2 of Example 1. pTG1166 (GUY et al, 1987) was totally digested with HindIII and partially cut with XhoI. The 1.2 kb XhoI-HindIII fragment, containing the pL promoter from phage Lambda and the complete Nef protein-encoding sequence (nef), was purified from agarose gel. Ends were filled in with Klenow polymerase. The fragment was then inserted in the ScaI site of pRR3 in both orientations to give rise to pWRIP1 and pWRIP2.

Figure 3A:
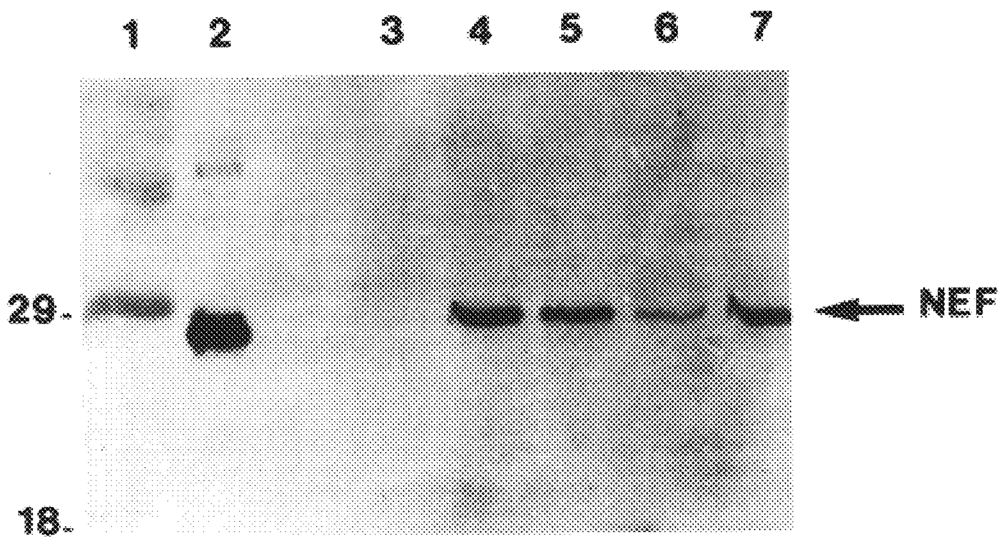

FIG. 3. Western blot analyses of recombinant *M. smegmatis* and *M. bovis* BCG clones of Example 1:

FIG. 3A: Proteins from *M. smegmatis* recombinant clones carrying pWRIP1 (lanes 4 and 5) and pWRIP2 (lanes 6 and 7) were extracted and separated in a 10% SDS-polyacrylamide gel. After electroblotting, membranes were reacted with a monoclonal antibody directed to HIV-1 Nef protein. Molecular weight marker appears on lane 1, and positive control containing purified Nef protein (27 kD) is shown on lane 2. Lane 3 contains an extract from non-recombinant *M. smegmatis* as a negative control. The lower amount of Nef protein observed in lane 6 was attributed to a lower amount of total proteins in this extract.

Figure 3B:
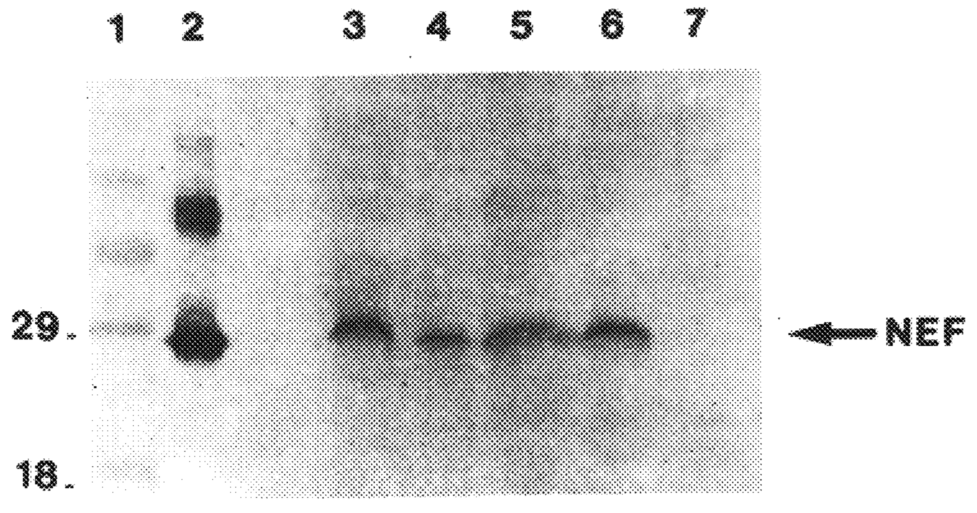

FIG. 3B: Proteins were extracted from *M. bovis* BCG recombinant clones carrying pWRIP1 (lanes 3 and 4) and pWRIP2 (lanes 5 and 6). Western blot analysis was, performed as described for FIG. 3A. Molecular weight marker and positive control appear on lanes 1 and 2, respectively. Extract of non-recombinant BCG as negative control is shown on lane 7.

Figure 4:
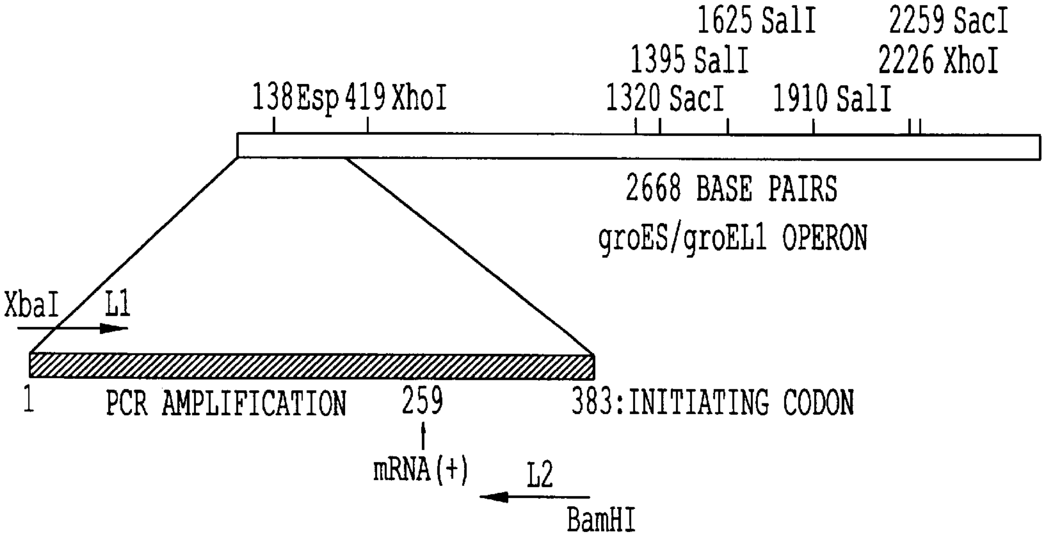

FIG. 4. A schematic representation of PCR amplification of Example 2. The groES/groEL1 region with its unique restriction sites is represented as a white box. The primers L 1 (5'CCCAGTACTCTAGACCGGCCGGGCTGAGGTTGGCTGGCT-3') (SEQ ID NO:2) and L2 (5'CCCCATATGGATCCCTCCCCCTTCGGAGATCACGGGGTT-A 3')(SEQ ID NO:3), used for amplification of the promoter region, are represented by arrows, and the amplification product is represented by a black box. The positions of the initiation of transcription and translation are shown. XbaI and BamHI unique sites, introduced with L1 and L2, allowed the cloning of the PCR product into a Blue Script vector to give pWRIP5.

Figure 5:
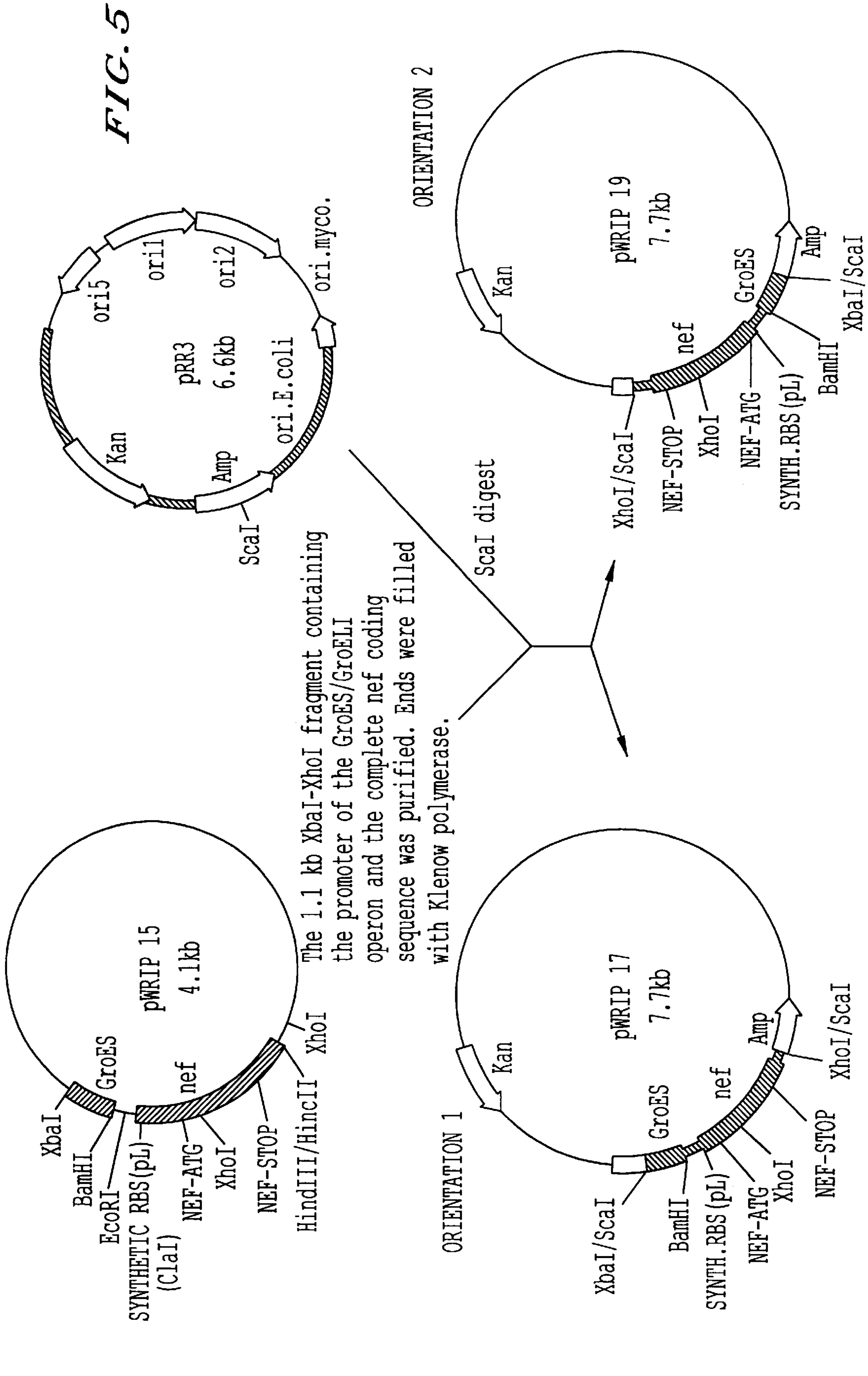

FIG. 5. Construction of pWRIP17 and pWRIP19 of Example 2. pWRIP15, which contains the groES/groEL1 PCR amplified promoter (French application 9011186) and nef gene with the synthetic ribosome binding site from pTG1166, was cut with XbaI and XhoI. The 1.1 kb fragment containing the groES/groEL1 promoter and nef expression cassette was purified from agarose. Ends were filled in with Klenow polymerase and ligated to pRR3 cut with ScaI. Recombinant plasmids, pWRIP17 and pWRIP19, carrying the cassette inserted in both orientations, were isolated from $kan^r$ *E. coli* cells.

Figure 6A:
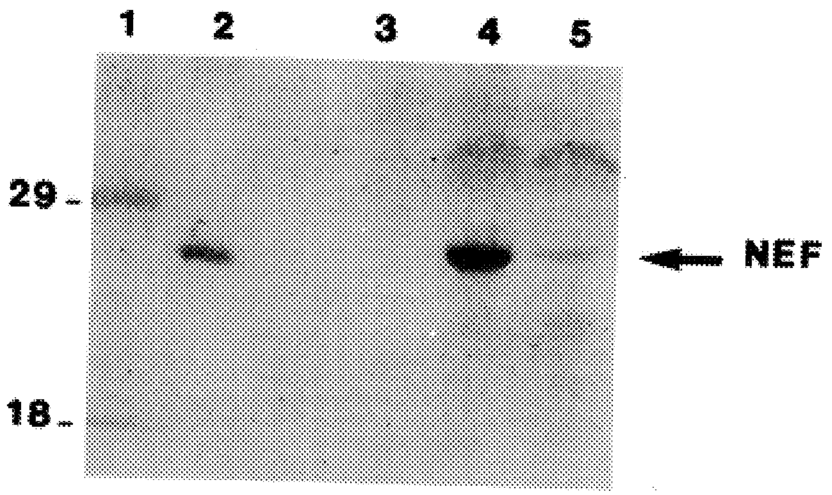

FIG. 6. Western blot analyses of *E. coli* and *M. bovis* BCG recombinant clones carrying pWRIP17 and pWRIP19 of Example 2:

FIG. 6A: 10 μg of total proteins from non-recombinant *E. coli* cells (lane 3) and *E. coli* transformed with plasmids pWRIP17 (lane 4) and pWRIP19 (lane 5) were extracted and separated with a 10% SDS-polyacrylamide gel. Western blot analysis was performed using a monoclonal anti-Nef antibody. Molecular weight marker and purified Nef protein (0.5 μg) appear on lanes 1 and 2, respectively.

Figure 6B:
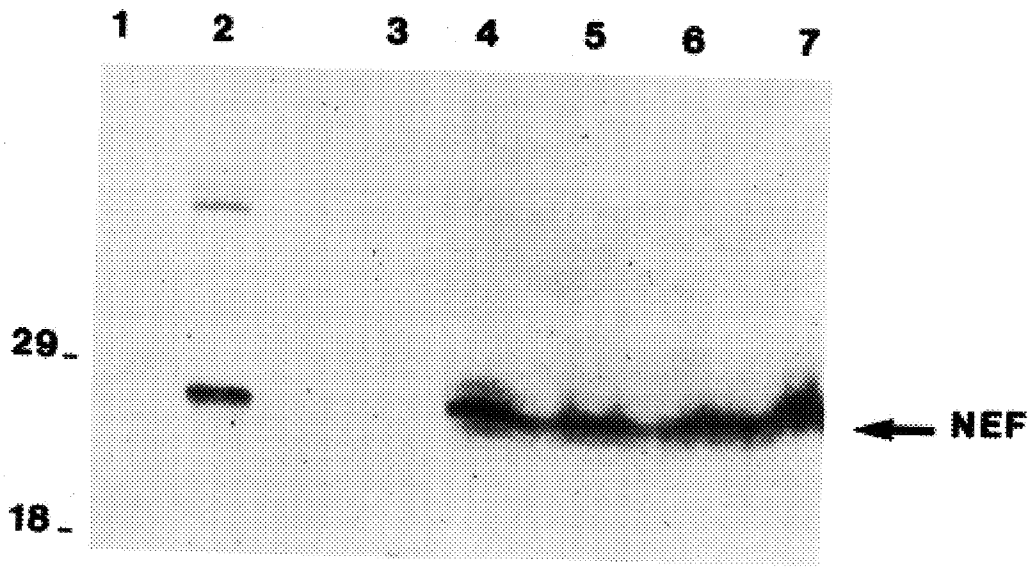

FIG. 6B: 100 μg of total proteins extracted from recombinant *M. bovis* BCG clones carrying pWRIP17 (lanes 4 and 5) and pWRIP19 (lanes 6 and 7) were analyzed as described for FIG. 6A. Negative control containing proteins from non-recombinant BCG appear on lane 3. Molecular weight marker and purified Nef protein are shown on lanes 1 and 2, respectively.

Figure 7:
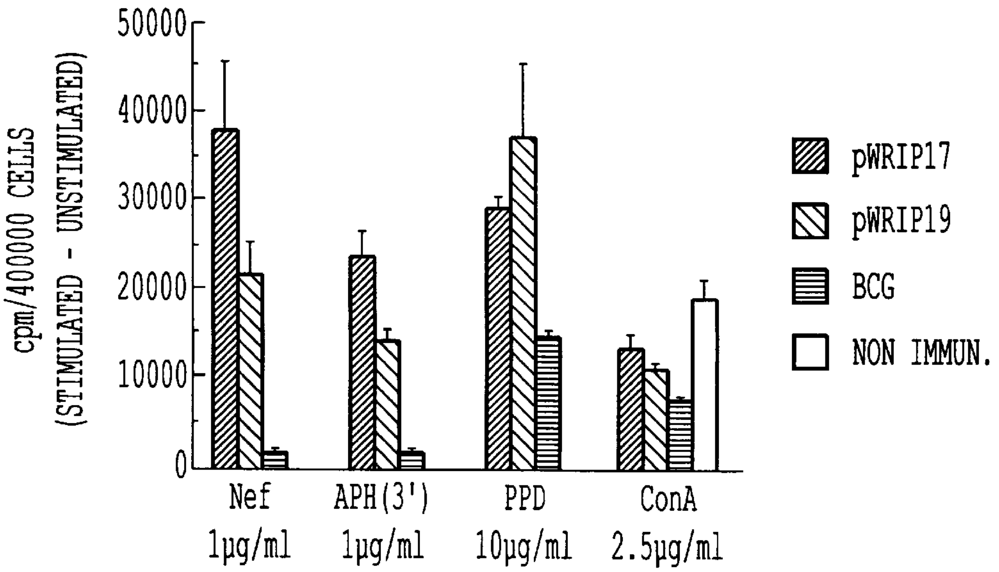

FIG. 7. Lymph node ("LN") proliferative response of Balb/c immunized mice in Example 3. Balb/c mice were injected s.c. with $10^7$ CFU of standard 1173P2 BCG (GHEORGHIU et al, 1983) or recombinant BCG carrying either pWRIP17 or pWRIP19 of Example 2. LN cells were stimulated with antigens before incorporation of tritiated methyl thymidine (($^3$H)dThd). The responses depicted are the geometrical means of results from three individuals for each animal group. The LN cells from non-immunized mice only responded to concanavalin A.

MATERIALS AND METHODS

1. Construction of Plasmids

DNA fragments were extracted from agarose gels by using the Gene Clean II kit (Bio 101 Inc., USA) or the Mermaid kit (Bio 101) depending on the length of the fragment to be purified.

Standard procedures were used for DNA ligation, restriction enzyme digestion and transformation in *E. coli* strains (SAMBROOK et al, 1989).

2. Bacterial Strains and Cultures

*E. coli* XL1 Blue strain (BULLOCK et al, 1987) was grown at 37° C. in L broth medium (MILLER et al, 1972). *E. coli* TGE901 (Transgene of Strasbourg, France), containing the thermosensitive repressor c1857 of phage lambda, was described by GUY. et al, 1987. The transformed *E. coli* cells were grown at 30° C. in L broth, and a two-hour shift at 42° C. was performed to induce expression of Nef protein under control of the phage lambda promoter.

*M. bovis* BCG (Institut Pasteur, Paris, France; GHEORGHIU et al, 1983 and *M. smegmatis* $mc^2$ 155 (SNAPPER et al, 1990) were transformed with the various recombinant plasmids by electroporation as described by RANES et al (1990).

Two methods of culture were used for BCG recombinant cell preparations. Firstly, the BCG recombinant, as well as a reference BCG strain, were grown in dispersed cultures (GHEORGHIU et al, 1988). BCG clones transformed with the various recombinant plasmids were grown on Lowenstein-Jensen medium containing 10 μg of kanamycin per ml. The kanamycin resistance gene from Tn903 (OKA et al, 1981) was used as a selective marker; it encodes an APH(3') phosphotransferase which is able to phosphorylate kanamycin but has no effect on tobramycin. Therefore, transformant clones were identified by their resistance to kanamycin and sensitivity to tobramycin. Two clones of each recombinant BCG strain were grown in modified Beck-Proskauer medium (GHEORGHIU et al, 1988) complemented with 10 μg of kanamycin per ml. The bacterial content of 10 days old cultures was $10^9$ colony forming units (CFU) per ml. Strains expressing the cloned chimaeric DNA sequence of this invention were inoculated into mice.

3. Preparation of Total Cellular Extracts

*E. coli* strains extracts were prepared from 5 ml cultures grown overnight in L broth. *M. smegmatis* $mc^2$ 155 strains were grown in Beck-Proskauer medium supplemented with Tween 80 (0.005%) and OADC (Difco), using the same culture conditions as previously described for *M. bovis* BCG strain. For recombinant cultures containing plasmids derived from pRR3, 25 μg of kanamycin per ml were added.

Cells were centrifuged at 3000 rpm for 10 min. at 4° C., and pellets were washed in TE buffer (10 mM Tris, pH 8; 1 mM EDTA). Pellets were then resuspended in 0.3 ml of TE buffer and frozen at −20° C. for 10 min. Cells were sonicated for 15 sec. periods during 1 min. 1% SDS was then added, and the extract was boiled 3 min. Cell extracts were centrifugated at 11000 rpm for 10 min. at 4° C., and supernatants were collected. When necessary, proteins were concentrated with acetone on ice for 30 min. and resuspended in a small volume of TE buffer. Amounts of proteins contained in the extracts were measured using the BIORAD microprocedure standard assay.

4. Electroporation of Mycobacteria

Exponential cultures of mycobacteria were washed, resuspended ($10^8$ to $10^9$ bacteria/ml) in 10% sucrose, 8 mM HEPES, pH 7.4, and 1 mM $MgCl_2$, chilled on ice for 30 min. and electroporated at 6.25 Kv/cm, 25 μF using the BIORAD Gene Pulser. Cultures were then diluted 10 times in Middlebrook 7H9 (Difco), incubated for about 12 hours at 37° C. and plated.on Middlebrook 7H10 (Difco) containing 10 to 40 μg/ml kanamycin. *M. smeamatis* transformants appeared after 5 days, and BCG transformants appeared after three weeks.

5. Western Blot Analysis

10 μg *E. coli* extracts or 100 μg mycobacterial extracts of soluble proteins were separated with SDS-polyacrylamide 10% gels (LAEMMLI, 1970). 10 μg of molecular weight marker proteins (Bethesda Research Laboratories) and 1 μg of purified recombinant *E. coli* Nef protein (Transgene), as positive control, were loaded on the gels.

After separation, polyacrylamide gels were electroblotted onto Immobilon membranes (Millipore, Corp.) using a Semiphor TE70 apparatus (Hoeffer Scientific Instruments). Non-specific binding was blocked by incubating the membranes in PBS (10 mM sodium phosphate; 150 mM NaCl, pH 7) at room temperature (25° C.) with 3% non-fat milk powder and 0.1% Tween 20, for 15 min. at room temperature. The proteins were then reacted over night with a 1:1000 diluted monoclonal antibody directed to Nef protein (NEN from Dupont). The membranes were washed three times for 10 min. each time with PBS and 0.1% Tween 20 and reacted with phosphatase alkaline-conjugated goat anti-mouse IgG (BIOSYS) at a 1:1000 dilution for 1 h at room temperature. After three times washing for 10 min each time with PBS and 0.1% Tween 20, the blots were reacted as described in Protoblot procedure (Promega).

6. Immunization of Mice

Female Balb/c mice (8 weeks) were immunized subcutaneously (sc) at the base of the tail with incomplete Freund adjuvant (IFA from DIFCO) containing $10^7$ colony forming units (CFU) of recombinant BCG strains or standard *M. bovis* BCG 1173 P2. After 14 days, draining inguinal lymph nodes were removed, and cell suspensions, pooled from three mice, were prepared (ANDERSEN et al, 1991). A single cell suspension of LN was prepared in RPMI 1640 (GIBCO) containing 2 mM L-glutamine, 50 μg/ml gentamycin, $5\times10^{-5}$M 2-mercaptoethanol, and 10% fetal calf serum (FCS). T-cells were cultivated at a concentration of $4\times10^5$ cells/well in 96-well flat bottom culture plates in the presence of the appropriate antigen. Concentration of the antigens added in cell cultures was on the basis of dose stimulation response as follows: Nef, $_1$ and 10 μg/ml; APH(3') 0.1 and 1 μg/ml; Protein Purified Derivative (PPD), 10 μg/ml; and Concanavalin A (ConA from Sigma), 2.5 μg/ml. Some cells were left unstimulated. Each test was performed in triplicate. Cultures were incubated for 5 days at 37° C. in humidified air with 7% $CO_2$, the last 22 h in the presence of tritiated methyl thymidine ($^3$H)dThd (1 mCi/ml). The cells were harvested on glass fiber filters with Automash 2000 Dynatech (Bioblock, France), and the incorporated radioactivity was measured in liquid scintillation counter (Beckman). The results are expressed as mean counts per minute (cpm) minus background.

EXAMPLE 1

Expression of HIV-1 Nef-encoding gene Under the Control of the lambda Phage pL Promoter pRR3 (RANES et al, 1990) was chosen as a vector for the cloning of the nef gene in *M. bovis* BCG. Its structure is shown in FIG. 1. It contains a pAL5000 2.58 kb fragment essential for replication and maintenance in mycobacteria, the $Kan^r$ gene from Tn903, and a pUC19 fragment harbouring an *E. coli* origin of replication. This plasmid was shown to be stable in *M. bovis* BCG when the bacteria are grown in in vitro laxenic cultures or in mice.

The Nef-encoding gene was previously cloned on the pTG1166 plasmid and expressed in *E. coli* under the control of the pL promoter of phage lambda (GUY et al, 1987). Since several gram-negative bacterial genes, such as antibiotic resistances, are expressed in mycobacteria under control of their own regulation signals, nef expression has also been examined in *M. smegmatis* and *M. bovis* BCG under pL control. The nef gene, containing a XhoI-HindIII fragment of pTG1166, was inserted into pRR3 at the ScaI site giving rise to pWRIP1 and pWRIP2, according to the orientation of the fragment (FIG. 2). These plasmids were transferred into *M. smegmatis* $mc^2$-155 strains by electroporation. *M. Smegmatis* kanamycin resistant (Kanr) transformant clones were examined for nef expression by western blot analyses. As shown in FIG. 3A, with both. orientations of the nef containing fragment in pRR3, expression of nef was observed, suggesting that the pL promoter is active in mycobacteria.

When pWRIP1 and pWRIP2 were transferred into *M. bovis* BCG by electroporation, expression of nef was also detected, albeit to a lesser extent (FIG. 3B).

EXAMPLE 2

Expression of HIV-1 Nef-encoding gene under the control of *S. albus* groES/groEL1 promoter In order to obtain a higher expression of nef in mycobacteria, this gene was cloned under the control of a stress-responsive promoter from Streptomyces (*S. albus*), a genus closely related to Mycobacteria. The aim was to induce an immune response to the Nef protein after inoculation of mice with *M. bovis* BCG recombinants harboring the nef gene. It was considered essential to clone nef under the control of a promoter which would be active when *M. bovis* replicates within macrophages so that the Nef antigen (s) would be expressed in the macrophages. The nef gene was therefore cloned under the control of a Streptomyces heat-shock promoter.

In order to examine the transcription of the *S. albus* groEL2 and groES/groEL1 promoters (French application 9011186; Appendix A) in mycobacteria, they were first fused to the kanamycin resistance gene from Tn5 encoding APH (3') phosphotransferase. High levels of kanamycin resistance (up to 5 mg/ml) were obtained in both *M. smegmatis* and *M. bovis* after electroporation with the recombinant plasmid constructions. However, Western blot analysis revealed that the groES/groEL1 promoter was more efficient.

A DNA fragment containing the promoter and the translation initiation control region of the groES/groEL1 region was synthesized by PCR using primers L1 and L2 containing respectively single XbaI and BamHI restriction sites. The fragment was then inserted into a Blue Script vector (Pharmacia, Sweden) to give pWRIP5 (FIG. 4). The HIV-1 BamHI-HindIII nef-containing fragment was then subcloned into pWRIP5 between BamHI and HindIII sites. The resulting plasmid pWRIP5F contained the entire nef coding sequence following the ATG start codon of the groES gene. The groES promoter and nef coding sequence XbaI-HindIII fragment from pWRIP5F was inserted into the ScaI site of pRR3 in both orientations. The resulting plasmids pWRIP7 and pWRIP9 were electroporated into *M. smegmatis* and *M. bovis* BCG. Neither *M. smegmatis* nor *M. bovis* BCG transformants expressed Nef. This result could be attributed to the 8-base pair changes introduced inside the groES/groEL1 translation controlling region during the cloning.

Since the nef gene was expressed in mycobacteria under the control of pL promoter associated with a synthetic ribosome binding site, the ClaI-HindlIl fragment of pTG1166 containing this element was inserted into pWRIP5 (FIG. 5). This resulted in plasmid pWRIP15. The XbaI-XhoI fragment from pWRIP15 was then subcloned into the ScaI site of pRR3 in both orientations to give pWRIP17 and pWRIP19. On these two plasmids, the nef gene is under-the control of the *S. albus* groES/groEL1 promoter and a synthetic ribosome binding site. pWRIP17 in *E. coli* was deposited at the Collection Nationale de Cultures de Microorganismes (CNCM) of Institut Pasteur under accession no. I-1109 on Jun. 6, 1991.

A high level of Nef synthesis was observed in *E. coli* cells transformed with pWRIP17. However, no expression of nef gene was detected in *E. coli* cells transformed with pWRIP19 (FIG. 6A). This result could be due to the ampicillin resistance ($Amp^r$) gene, the promoter of which was cloned in an opposite direction to nef and which might down-regulate its expression. A high level of Nef synthesis was observed in M. smegmatis and in *M. bovis* BCG bacteria transformed with pWRIP17 and pWRIP19 (FIGS. 6A and 6B). The Nef protein was estimated to be about 1% of the total cellular protein. Nef was shown to be expressed in *M. bovis* BCG cultured in various growth conditions: in dispersed grown cultures and in Sauton cultures. In addition, expression of the APH(3') phosphotransferase was also detected by Western blot analysis in the different *M. bovis* BCG culture preparations.

EXAMPLE 3

Determining proliferative responses to Nef and to APH3 ' antigens in mice immunized with recombinant *M. bovis* BCG Balb/c mice were immunized by subcutaneous inoculation with recombinant *M. bovis* BCG harboring plasmids pWRIP17 and pWRIP19 from Example 2. Cellular responses were investigated by examining the proliferative response of cells isolated from lymph nodes (LN). These cells were cultured in vitro and stimulated with purified Nef or APH(3'). As shown in FIG. 7, LN cells isolated from mice immunized with Nef- and APH(3')-recombinant *M. bovis* BCG strongly proliferated to purified Nef or APH(3'). This proliferation was highly specific since mice immunized with non-recombinant BCG or with incomplete Freund adjuvant alone did not respond to these heterologous proteins.

In contrast, the proliferation to PPD was comparable in all mice inoculated with non-transformed *M. bovis* BCG and recombinant strains (FIG. 7). No significant proliferation was observed in LN cells isolated from non-immunized mice. The non-specific proliferative responses of LN cells to concanavalin A (ConA) was the same in all animals.

These results show that, after inoculation in mice, expression of Nef and APH(3') in recombinant BCG induces the specific proliferation of LN cells from immunized mice.

REFERENCES

Aldovini, A. and Young, R.: Humoral and cell-mediated immune responses to live recombinant BCG-HIV vaccines. Nature 351 (1991) 479–482.

Amrann, E., Brosius, J. and Ptashne, M.: Vectors bearing a hybrid tip-loc promoter useful for requested expression of cloral genes in *E. coli*. Gene 25 (1983) 167–178.

Andersen, P., Asgaard, D., Ljungvist, L., Weis-Bentzon, M. and Heron, I.: T-cell proliferative response to antigens by *Mycobacterium tuberculosis*. Infect. Immun. 59 (1991) 1558–1563.

Bloom, B. R.: Learning from leprosy: a perspective on immunology and the third world. J. Immunol. 137 (1986) I–X.

Brown, A., Hormaeche, C. E., Demarco de Hormaeche, R., Winther, M., Dougan, G., Maskell, D. J., and Stocker, B. A. D.: An attenuated aroA *Salmonella typhimirium* vaccine elicits humoral and cellular immunity to cloned B-galactosidase in mice. J. Infect. Dis. 155 (1987) 86–92.

Buchmeier, N. A. and Heffron, F.: Induction of Salmonella stress proteins upon infection of macrophages. Science 248 (1990) 730–732.

Bullock, W. O., Fernandez, J. M. and Short, J. M.: XL1 Blue: a high efficiency plasmid transforming recA *Escherichia coli* strain with betagalactosidase selection. Biotechniques. 5 (1987) 376–379.

Colston, M. J.: Protective immunity against mycobacterial infections: investigating cloned antigens. In Molecular biology of the mycobacteria. Ed. J. Mc Fadden, Surrey University Press 69–76.

Culmann, B., Gomard, E., Kieny M. P., Guy, B., Dreyfus, F., Saimot, A. G., Sereni, D. and Levy J. P.: An antigenic peptide of the HIV-1 Nef protein recognized by cytotoxic T lymphocytes of seropositive individuals in association with different HLA-B molecules. Eur. J. Immunol. 19 (1989) 2383–2386.

Edwards, D. and Kirkpatrick, H.: The immunology of mycobacterial diseases. Am. Rev. Resp. Dis. 134 (1986) 1062–1071.

Garcia, J. V. and Miller, A. D.: Serine phosphorylation-independent down regulation of cell-surface CD4 by nef. Nature 350 (1991) 508–511.

Gheorghiu, M., Lagrange, P. H. and Fillastre, C.: The stability and immunogenicity of a dispersed grown freeze derived Pasteur BCG vaccine. J. Biol. Stand. 16 (1988) 15–26.

Gheorghiu, M., Augier, J. and Lagrange, P. H.: Maintenance and control of the French BCG strain 1173-$P_2$ (primary and secondary seed lots). Bull. Inst. Pasteur 81 (1983) 281–288.

Gicquel-Sanzey, B., Moniz-Pereira, J., Gheorgiu, M. and Rauzier, J., Acta Leprologica 7 (1989) 208–211.

Guy, B., Kieny, M. P., Riviere, Y., Le Peuch, C., Dott, K., Girard, M., Montagnier, L. and Lecoq J. P.: HIV F/3'orf encodes a phosphorylated GTP-binding protein ressembling an oncogene product. Nature 330 (1987) 266–269.

Jacobs, W. R. Jr., Snapper, S. B. and Bloom, B. R.: In Molecular biology and infectious diseases. Ed. M. Schartz, Elsevier, New-York (1988) 207–212.

Laemmli, U. K.: Cleavage of structural proteins during the assembly of the head of bacteriophage T4. Nature 227 (1970) 680–685.

Lazraq, R., Seres-Clavel, S., David, H. L. and Roulland-Dussoix, D.: Conjugative transfer of a shuttle plasmid for *Escherichia coli* to *Mycobacterium smegmatis*. FEMS Microbiol. Lett. 69 (1990) 135–138.

Leclerc, C., Charbit, A., Molla, A. and Hofnung, M.: Antibody response to a foreign epitope expressed at the surfact of recombinant bacteria: importance of the route of immunization. Vaccine 7 (1989) 242–248.

Martin, C., Timm, J., Kauzier, J., Gomez-Luis, R., Davies, J. and Gicquel, B.: Transposition of an antibiotic resistance element in mycobacteria. Nature 345 (1990) 739–743.

Matsuo, K., Yamaguchi, R., Yamazaki, A., Tasaka, H., Terasaka, K., Totsuka, M., Kobayashi, K., Yukitake, H. and Yamada, T.: Establishment of foreign antigen secretion system in mycobacteria. Infect. Immun. 58 (1990) 4049–4054.

Miller, J. H.: Experiments in molecular genetics. Cold Spring Harbor Laboratory, Cold Spring Harbor, N.Y. (1972) Mustafa, A. S., Kaur-Gill, H., Nerland, A., Britton, W. J., Mehra, V., Bloom, B. R., Young, R. A. and Godal, T.: Human T-cell clones recognize a major *M. Leprae* protein antigen expresses in *E. coli*. Nature 312 (1986) 63–66.

Oka, A., Sugisaki, H., and Takanami, M.: Nucleotide sequence of the kanamycin resistance transposon Tn 903. J. Mol. Biol. 147 (1981) 217–226.

Ranes, M. G., Rauzier, J. Lagranderie, M., Gheorghiu, M. and Gicquel, B.: Functional analysis of pAL5000, a plasmid from *Mycobacterium fortuitum*: construction of a "mini" mycobacterium-*Escherichia coli* shuttle vector. J. Bact. 172 (1990) 2793–2797.

Rauzier, J., Moniz-Pereira, J. and Gicquel-Sanzey, B.: Complete nucleotide sequence of pAL5000, a plasmid from *Mycobacterium fortuitum*. Gene 71 (1988) 315–321.

Riviere, Y., Tanneau-Salvadori, F., Regnault, A., Lopez, O., Sansonetti, P., Guy, B., Kieny, M. P., Fournel, J. J. and Montagnier, L.: Human immunodeficiency virus-specific cytotoxic responses of seropositive individuals: distinct types of effector cells mediate killing of targets expressing Gag and Env proteins. J. Virol. 63 (1989) 2270–2277.

Sambrook, J., Fritsch, E. F. and Maniatis, T.: Molecular cloning. A laboratory manual 2nd edn. Cold Spring Harbor Laboratory, Cold Spring Harbor, N.Y., 1989.

Snapper, S. B., Melton, R. E., Mustafa, A. S. and Jacobs, W. R.: Isolation and characterization of efficient plasmid transformation mutants of *Mycobacterium smegmatis*. Mol. Microbiol. 4 (1990) 1911–1919.

Stover, C. K., de la Cruz, V. F., Fuerst, T. R., Burlein, J. E., Benson, L. A., Bennett, L. T., Bansal, G. P., Young, J. F., Lee, M. H., Hatfull, G. F., Snapper, S. B., Barletta, R. G., Jacobs, W. R. Jr and Bloom, B. R.: New use of BCG for recombinant vaccines. Nature 351 (1991) 456–460.

Walker, B. D. and Plata, F.: Cytotoxic T lymphocytes against HIV. AIDS 4 (1990) 177–184.

Young, D., Garbe, T., Lathigra, R. and Abou-Zeid, C.: Protein antigens: structure, function and regulation. In Molecular biology of the mycobacteria. Ed. J. Mc Fadden, Surrey University Press (1990) 1–35.

What is claimed is:

1. An immunogenic strain of Actinomycetale comprising a recombinant DNA, wherein said recombinant DNA includes a gene, said gene includes a promoter from a strain different from that of said Actinomycetale strain or from a species different from that of said Actinomycetale strain, and a synthetic ribosome binding site, said gene is capable of being expressed in said immunogenic strain, said gene encodes a protein that is foreign to the species to which said immunogenic strain belongs, and said protein elicits an immune response in a mammal.

2. The strain of claim 1, wherein said ribosome binding site includes the sequence of SEQ ID NO: 1.

3. The strain of claim 1, wherein said protein is an HIV-1 protein.

4. The strain of claim 3, wherein said HIV-1 protein is the Nef protein.

5. The strain of claim 1, which is Mycobacterium.

6. The strain of claim 5, wherein said Mycobacterium is selected from the group consisting of *Mycobacterium tuberculosis* and *Mycobacterium bovis* BCG.

7. A process for producing a protein eliciting an immune response in an animal, comprising the steps of (a) culturing said immunogenic strain of claim 1 under conditions sufficient to allow said protein to be produced; and (b) recovering the immunogenic strain cultured in step (a).

8. A process for producing said immunogenic strain of claim 1, comprising the steps of (a) electroporating a cell of a strain of Actinomycetale with a recombinant DNA, wherein said recombinant DNA includes a gene, said gene includes a promoter from a strain different from that of said Actinomycetale strain or from a species different from that of said Actinomycetale strain, and a synthetic ribosome binding site, said gene is capable of being expressed in said Actinomycetale strain, said gene encodes a protein that is foreign to the species to which said Actinomycetale strain belongs, and said protein elicits an immune response in a mammal; and (b) recovering said immunogenic strain.

9. The strain of claim 1, wherein said recombinant DNA is integrated into the chromosome of said immunogenic strain.

10. The strain of claim 1, wherein said recombinant DNA is in a plasmid.

11. A recombinant DNA capable of transforming cells of a strain of Actinomycetale, wherein said recombinant DNA includes a gene, said gene includes a promoter from a strain different from that of said Actinomycetale strain or from a species different from that of said Actinomycetale strain, and a synthetic ribosome binding site, said gene is capable of being expressed in said immunogenic strain, said gene encodes a protein that is foreign to the species to which said immunogenic strain belongs, and said protein elicits an immune response in a mammal.

12. The recombinant DNA of claim 11, wherein said protein is an HIV-1 protein.

13. The recombinant DNA of claim 11, wherein said Actinomycetale strain to be transformed is Mycobacterium.

14. The recombinant DNA of claim 11, wherein said recombinant DNA is a plasmid.

15. The recombinant DNA of claim 14, wherein said plasmid is selected from the group consisting of pWRIP1, pWRIP2, pWRIP 17, and pWRIP 19.

16. The recombinant DNA of claim 11, wherein said Streptomyces promoter is the groES/groEL1 promoter of *Streptomyces albus*.

17. A vector capable of transforming a strain of Actinomycetale, comprising a promoter from a strain different from that of said Actinomycetale strain or from a species different from that of said Actinomycetale strain and a synthetic ribosome binding site, said gene is expressed in said immunogenic strain, said gene encodes a protein that is foreign to the species to which said immunogenic strain belongs, and said protein elicits an immune response in a mammal.

18. An immunogenic strain of Actinomycetale, comprising a recombinant DNA, wherein said recombinant DNA includes a gene, said gene includes a promoter selected from the group consisting of: an Actinomycetale strain that is different from said immunogenic strain of Actinomycetale, an Actinomycetale species that is different from the species of said immunogenic strain of Actinomycetale, a phage lambda promoter and an antibiotic resistance gene promoter, said gene is expressed in said immunogenic strain, said gene encodes a protein that is foreign to the species to which said immunogenic strain belongs, and said protein elicits an immune response in a mammal.

19. A process for producing said immunogenic strain of claim 18, comprising (a) electroporating a cell of a strain of Actinomycetale with a recombinant DNA, wherein said recombinant DNA includes a gene, said gene includes a promoter selected from the group consisting of: an Actinomycetale strain that is different from said immunogenic strain, an Actinomycetale species that is different from the species of said immunogenic strain, a phage lambda promoter and an antibiotic resistance gene promoter, said gene is expressed in said immunogenic strain, said gene encodes a protein that is foreign to the species to which said immunogenic strain belongs, and said protein elicits an immune response in a mammal; and (b) recovering said immunogenic strain.

20. The strain of claim 18, wherein said promoter is a Streptomyces promoter.

21. The strain of claim 20, wherein said Streptomyces promoter is the groES/groE11 promoter of *Streptomyces albus*.

22. The strain of claim 18, wherein said promoter is selected from the group consisting of: a kanamycin resistance gene promoter, a bacterial promoter of the sulfanamide gene, and a bacterial TAC promoter.

23. The strain of claim 18, wherein said recombinant DNA is integrated into the chromosome of said immunogenic strain.

24. The strain of claim 18, wherein said recombinant DNA is extrachromosomal.

25. A recombinant DNA capable of transforming cells of a specific strain of Actinomycetale, wherein said recombinant DNA includes a gene, said gene includes a promoter selected from the group consisting of: an Actinomycetale strain that is different from said specific strain of Actinomycetale, an Actinomycetale species that is different from the species of said specific strain of Actinomycetale, a phage lambda promoter and an antibiotic resistance gene promoter, said gene is expressed in the transformed Actinomycetale strain, said gene encodes a protein that is foreign to the species to which said transformed Actinomycetale strain belongs, and said protein elicits an immune response in a mammal.

26. The recombinant DNA of claim 25, wherein said phage lambda promoter is a pL promoter.

27. The recombinant DNA of claim 25, wherein said promoter is a Streptomyces promoter.

28. The recombinant DNA of claim 25, wherein said promoter is selected from the group consisting of: a kanamycin resistance gene promoter, a bacterial promoter of the sulfanamide gene, and a bacterial TAC promoter.

29. A vector capable of transforming a first strain of Actinomycetale, comprising; a promoter that is foreign to said first Actinomycetale strain and which functions to promote expression of a gene encoding a protein that is foreign to the species of said first Actinomycetale strain, and said protein elicits an immune response in a mammal.

30. The vector of claim 29, wherein said promoter is a Streptomyces promoter.

31. The vector of claim 29, wherein said promoter is selected from the group consisting of: a kanamycin resistance gene promoter, a bacterial promoter of the sulfanamide gene, and a bacterial TAC promoter.

* * * * *

UNITED STATES PATENT AND TRADEMARK OFFICE
CERTIFICATE OF CORRECTION

PATENT NO. : 6,235,518 B1
DATED : May 22, 2001
INVENTOR(S) : Gicquel et al.

It is certified that error appears in the above-identified patent and that said Letters Patent is hereby corrected as shown below:

Title page,
Item [87], the PCT Publication information should read:
-- [87] PCT Pub. No.: WO 92/22658
PCT Pub. Date: Dec. 23, 1992 --

Signed and Sealed this

Nineteenth Day of February, 2002

*Attest:*

JAMES E. ROGAN
*Director of the United States Patent and Trademark Office*

*Attesting Officer*

SEQUENCE LISTING

```
(1) GENERAL INFORMATION:

   (iii) NUMBER OF SEQUENCES: 3


(2) INFORMATION FOR SEQ ID NO:1:

     (i) SEQUENCE CHARACTERISTICS:
          (A) LENGTH: 23 base pairs
          (B) TYPE: nucleic acid
          (C) STRANDEDNESS: unknown
          (D) TOPOLOGY: unknown
```

-continued

```
    (ii) MOLECULE TYPE: Other nucleic acid

    (xi) SEQUENCE DESCRIPTION: SEQ ID NO:1:

ATCGATAACA GAGGAACAGA TCT                                              23


(2) INFORMATION FOR SEQ ID NO:2:

     (i) SEQUENCE CHARACTERISTICS:
          (A) LENGTH: 39 base pairs
          (B) TYPE: nucleic acid
          (C) STRANDEDNESS: unknown
          (D) TOPOLOGY: unknown

    (ii) MOLECULE TYPE: Other nucleic acid

    (xi) SEQUENCE DESCRIPTION: SEQ ID NO:2:

CCCAGTACTC TAGACCGGCC GGGCTGAGGT TGGCTGGCT                             39


(2) INFORMATION FOR SEQ ID NO:3:

     (i) SEQUENCE CHARACTERISTICS:
          (A) LENGTH: 39 base pairs
          (B) TYPE: nucleic acid
          (C) STRANDEDNESS: unknown
          (D) TOPOLOGY: unknown

    (ii) MOLECULE TYPE: Other nucleic acid

    (xi) SEQUENCE DESCRIPTION: SEQ ID NO:3:

CCCCATATGG ATCCCTCCCC CTTCGGAGAT CACGGGGTT                             39
```